United States Patent
McIntyre et al.

(10) Patent No.: US 10,112,049 B2
(45) Date of Patent: Oct. 30, 2018

(54) LOAD-PRESERVING METHOD FOR DEFINING ANISOTROPY IN VOLUME-CONDUCTOR MODELS

(71) Applicant: Case Western Reserve University, Cleveland, OH (US)

(72) Inventors: Cameron McIntyre, Cleveland, OH (US); Bryan Howell, Cleveland, OH (US)

(73) Assignee: Case Western Reserve University, Cleveland, OH (US)

(*) Notice: Subject to any disclaimer, the term of this patent is extended or adjusted under 35 U.S.C. 154(b) by 33 days.

(21) Appl. No.: 15/356,895

(22) Filed: Nov. 21, 2016

(65) Prior Publication Data

US 2017/0165489 A1    Jun. 15, 2017

Related U.S. Application Data

(60) Provisional application No. 62/265,125, filed on Dec. 9, 2015.

(51) Int. Cl.
| | | |
|---|---|---|
| *A61N 1/36* | (2006.01) | |
| *A61N 1/05* | (2006.01) | |
| *G06F 17/50* | (2006.01) | |
| *G16H 50/50* | (2018.01) | |

(52) U.S. Cl.
CPC ....... *A61N 1/36067* (2013.01); *A61N 1/0534* (2013.01); *G06F 17/50* (2013.01); *G16H 50/50* (2018.01)

(58) Field of Classification Search
CPC .. A61B 5/4041; A61B 5/053; G01R 33/4806; A61N 1/36067; A61N 1/0534; G16H 50/50; G06F 17/50
See application file for complete search history.

(56) References Cited

U.S. PATENT DOCUMENTS 7,346,382 B2 * 3/2008 McIntyre ........... A61N 1/36082
                                                    600/407

OTHER PUBLICATIONS

Güllmar, et al. "Influence of Anisotropic Electrical Conductivity in White Matter Tissue on the EEG/MEG Forward and Inverse Solution. A High-Resolution Whole Head Simulation Study." NeuroImage 51 (2010) 145-163. Published Feb. 13, 2010.

(Continued)

*Primary Examiner* — Alyssa M Alter
(74) *Attorney, Agent, or Firm* — Eschweiler & Potashnik, LLC

(57) ABSTRACT

Example systems and methods concern systems and methods for modeling conduction in a volume. In one embodiment, diffusion eigenvalues of a plurality of diffusion tensors are received. The diffusion tensors are associated with an anatomical structure having heterogeneous and anisotropic tissues. In one embodiment, the diffusion eigenvalues of the diffusion tensors are calculated from imaging data. Then one or more conductance ratios of a conductivity tensor are set based, at least in part, on one or more diffusion ratios of a corresponding diffusion tensor. The conductance eigenvalues of a conductivity tensor can then be calculated based, at least in part, on the one or more conductance ratios of the conductivity tensor. A volume-conductor model of the anatomical structure is generated based, at least in part, on the plurality of calculated conductivity tensors.

18 Claims, 10 Drawing Sheets

(56) References Cited

OTHER PUBLICATIONS

Tuch, et al. "Conductivity Tensor Mapping of the Human Brain Using Diffusion Tensor MRI" PNAS, vol. 98, No. 20, 11697-11701. Published Sep. 25, 2001.

* cited by examiner

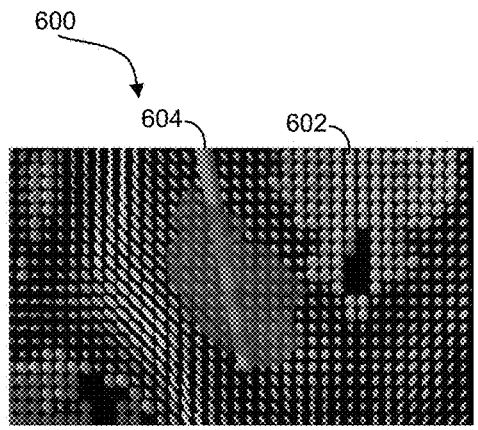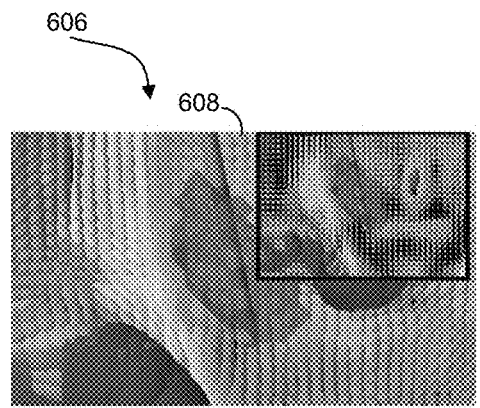
Fig. 6A　　　　　　　　Fig. 6B
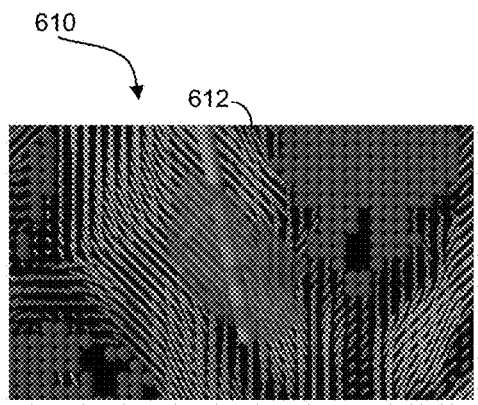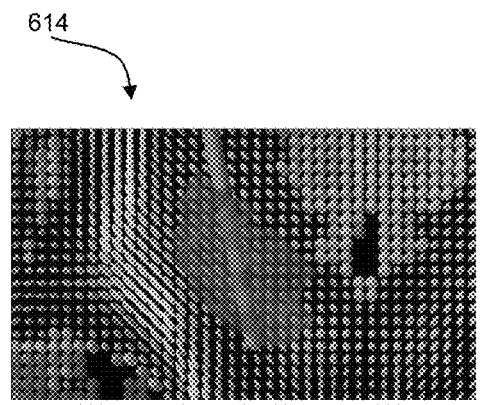
Fig. 6C　　　　　　　　Fig. 6D

LOAD-PRESERVING METHOD FOR DEFINING ANISOTROPY IN VOLUME-CONDUCTOR MODELS

CROSS-REFERENCE TO RELATED APPLICATIONS

This Application claims the benefit of U.S. Provisional Patent Application No. 62/265,125 filed Dec. 9, 2015, which is hereby incorporated by reference in its entirety.

FEDERAL FUNDING NOTICE

The invention was made with government support under Federal Grant No. MH102238 awarded by the National Institute of Mental Health. The government has certain rights in the invention.

BACKGROUND

Electrical stimulation of an anatomical region in electrically excitable tissue, such as a patient's brain, can mitigate symptoms in neurological disorders. In one embodiment, deep brain stimulation (DBS) is effective in treating the symptoms of patients with movement disorders. One example is DBS, where brief pulses of current are delivered to specific regions of the brain in order to modulate pathological network activity of those areas of the brain. For example, a small part of the thalamus is one target for treating essential tremor, and the subthalamic nucleus is another target for treating Parkinson's disease. Because treatment is based on applying the stimulation to a particular anatomical structure, or region thereof, efficacy of the treatment is based on the ability of a clinician to tailor the application of stimulation based on the particular anatomy of the patient.

BRIEF DESCRIPTION OF THE DRAWINGS

The accompanying drawings, which are incorporated in and constitute a part of the specification, illustrate various example devices, methods, apparatus and other embodiments of various aspects of the invention. It will be appreciated that the illustrated element boundaries (e.g., boxes, groups of boxes, or other shapes) in the figures represent one example of the boundaries. In some embodiments one element may be designed as multiple elements, multiple elements may be designed as one element, an element shown as an internal component of another element may be implemented as an external component and vice versa, and so on. Furthermore, elements may not be drawn to scale.

FIG. 6A illustrates an example of defining anisotropy in an anatomical structure, the brain, according to a load-preservation approach.

FIG. 6B illustrates an example of defining anisotropy in an anatomical structure, the brain, according to an approach that uses the Tuch cross-property relationship.

FIG. 6C illustrates an example of defining anisotropy in an anatomical structure, the brain, according to a classical approach.

FIG. 6D illustrates an example of defining anisotropy in an anatomical structure, the brain, according to a volume-conservation approach.

DETAILED DESCRIPTION

Figure 1:
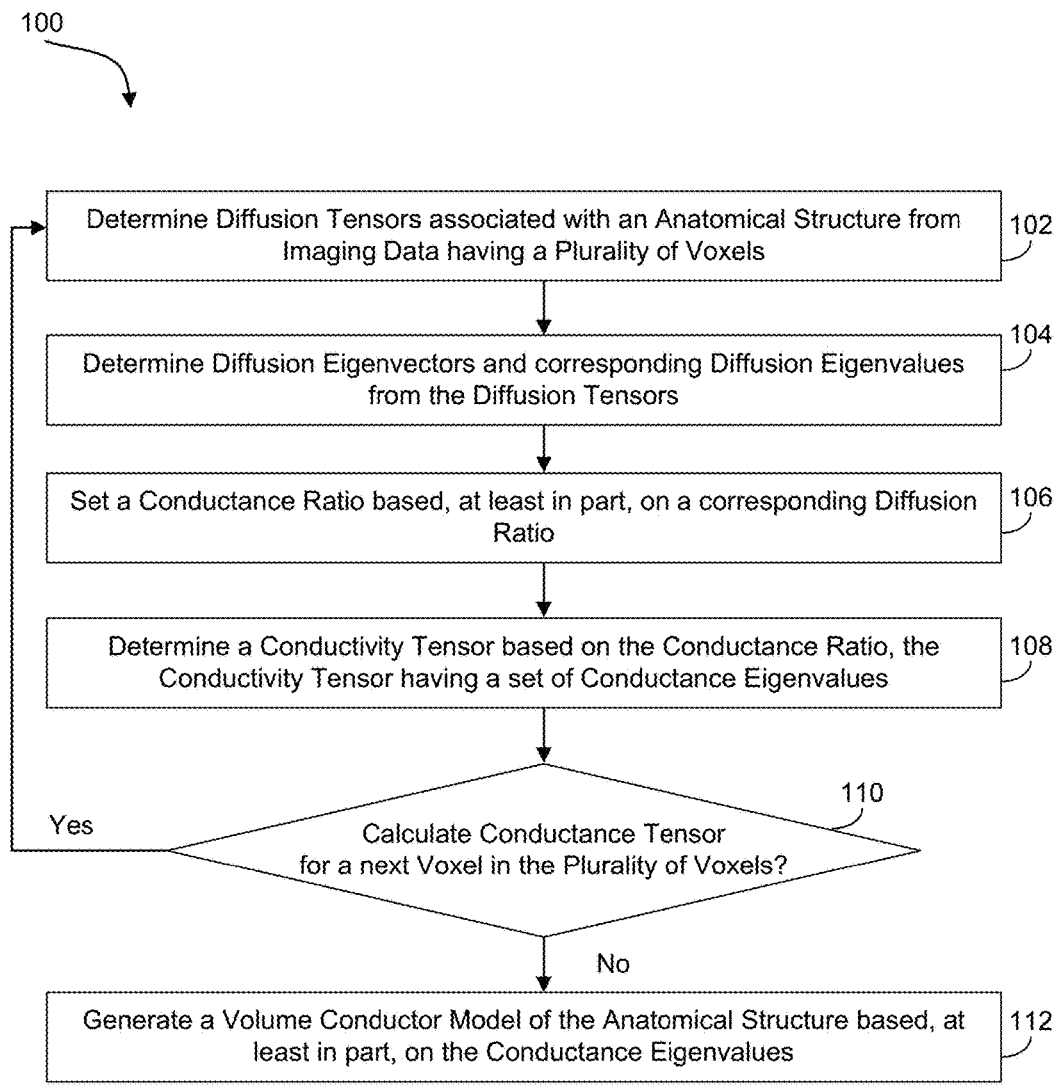
FIG. 1 illustrates an example method associated with defining the electrical properties of a volume-conductor model including steps for defining eigenvectors of a conductivity tensor based on eigenvectors of diffusion tensor.

Example systems and methods provide modeling of a volume conductor to simulate electrical stimulation of an anatomical structure of a patient. In particular, a clinician or physician stimulating the anatomical structure can tailor stimulation parameters to the patient based on his or her volume-conductor model. The stimulation parameters may include determining which one of the stimulating electrodes to use (i.e., electrode configuration), the stimulation pulse amplitude, the stimulation pulse width, the stimulation frequency, etc.

In one embodiment, volume-conductor models may be used for targeting of deep brain stimulation (DBS). The volume-conductor model may facilitate identifying potential therapeutic white matter targets for Parkinson's disease and/or prospectively selecting stimulation parameters that are more energy efficient and evoke less side effects than settings defined with traditional clinical practice. While the examples provided concern the treatment of Parkinson's disease, systems and methods described are more generally applicable to patients using stimulation systems for treatment of any illness or condition.

The volume-conductor model is based on the electrical properties of the anatomical structures that are modeled. For example, in DBS, the complexity of the volume-conductor model is, in part, based on the representation of heterogeneity and anisotropy in the tissues and regions constituting the brain. This is further complicated by the different electrical properties of grey matter, white matter, and cerebral spinal fluid (CSF) because there is no consensus on how to define anisotropy in these regions. Thus, tailoring the treatment to the patient is complicated by uncertainty in how to define the electrical properties of the anatomy of the patient (e.g., heterogeneity and anisotropy of tissues).

A volume-conductor model may rely on medical images, such as magnetic resonance (MR) images or computer tomography (CT) images, to tailor anatomical aspects of the volume-conductor model to the patient. For example, the Tuch Cross-Property Relationship (CPR) is one conventional approach that, uses values extracted from a diffusion-weighted MR image to define conductivity tensors in a volume-conductor model. Tuch CPR predicts conductivities (i.e., the eigenvalues of the conductivity tensor) in CSF that are consistent with what has been measured in vivo, but the conductivities predicted in grey matter and white matter are 2-3 times larger than the range of values reported in the literature. One can adjust the Tuch CPR so that predicted conductivities are more consistent, say, in grey matter, but at the expense of markedly misestimating the conductivities of white matter and CSF. Also, the Tuch CPR does not account for dielectric dispersion present in the electrical properties of the tissue.

Here, heterogeneity and anisotropy are accounted for in a volume-conductor model. Suppose that imaging data is received for a particular anatomical structure, such as the brain. Heterogeneity is incorporated in the volume-conductor model by subdividing the volumetric imaging data of the anatomical structure into component regions. For example, the volumetric image of the brain may be subdivided into white matter, grey matter, and CSF regions. The electrical properties of the brain can then be assigned based on the conductivities and permittivities specific to the aforementioned individual regions.

Anisotropy is also incorporated into the volume conductor model. A volumetric image of an anatomical structure includes a plurality of voxels, each having a diffusion tensor. Each diffusion tensor is, by definition, symmetric and thereby can be decomposed into three eigenvectors and corresponding eigenvalues. The eigenvectors and eigenvalues of a conductivity tensor are based on the eigenvectors and eigenvalues of the diffusion tensor. In one embodiment, one or more diffusion eigenvalue ratios are calculated from at least two diffusion eigenvalues of the set of diffusion eigenvalues. One or more eigenvalue ratios of the conductivity tensor are then determined based on the one or more eigenvalue ratios of the diffusion tensor. The eigenvalues of the conductive tensor can then be calculated based on the determined conductance eigenvalue ratios, an effective isotropic conductivity, and a mapping between isotropic conductivity and eigenvalues of the conductivity tensor. A volume-conductor model is generated based, at least in part, on the calculated eigenvalues of the conductivity tensor. Because the eigenvectors and eigenvalues of the diffusion tensors are derived from voxels imaging the anatomical structure, and thus, the calculated eigenvectors and eigenvalues of the conductivity tensors are specific to the anatomical structure, the volume-conductor model incorporates both heterogeneity and anisotropy of the anatomical structure. Accordingly, the bioelectric nature of anatomical structure can be more accurately modeled for the individual patient.

FIG. 1 illustrates an example method associated with defining the electrical properties of a volume-conductor model including steps for defining eigenvectors of a conductivity tensor based on eigenvectors of diffusion tensor.

At 102, diffusion tensors associated with an anatomical structure. The diffusion tensors represent the diffusion of water in the anatomical structure. As will be discussed in the following, the diffusion tensors may be determined from imaging data that is patient specific. Accordingly, any data derived from the diffusion tensors is also patient specific.

At 104, diffusion eigenvectors, and corresponding diffusion eigenvalues, are determined from the diffusion tensors. Suppose that the imaging data includes a plurality of voxels, and each voxel corresponds to a diffusion tensor. A set of diffusion eigenvalues is determined for each diffusion tensor. The set of diffusion eigenvalues of a diffusion tensor represent the diffusion characteristics of the anatomical structure imaged imaging data of a selected voxel associated with the diffusion tensor.

At 106, a conductance ratio is set equal to a diffusion ratio of the determined diffusion eigenvalues. For example, a diffusion ratio may be defined by at least two diffusion eigenvalues. In one embodiment, the diffusion ratio may be defined by at least two eigenvalues in a set of eigenvalues such that the diffusion ratio also corresponds to the selected voxel. Thus, a conductance ratio set to equal the diffusion ratio also corresponds to the selected voxel.

At 108, the conductance ratio is used to determine the conductivity tensor for the selected voxel. Because the conductivity tensor is determined from the corresponding diffusion tensor, the conductivity tensor is also patient specific. The conductivity tensor includes a set of conductance eigenvalues corresponding to the set of diffusion eigenvalues.

At 110, it is determined whether acts 102-108 are repeated for a next voxel in the plurality of voxels. In one embodiment, it is determined whether acts 102-108 are repeated based on a predetermined number of voxels of the plurality of voxels. In another embodiment, acts 102-108 are repeated until a conductance tensor is calculated for each voxel in the plurality of voxels. If it is determined that steps 102-108 are to be repeated, steps 102-108 are repeated until conductance tensors are calculated for the plurality of voxels of the imaging data. Each conductance tensor is associated with a set of conductance eigenvalues. of voxels. If it is determined that steps 102-108 are not to be repeated, the method proceeds to step 112.

At 112, a volume conductor model is generated based, at least in part, on the sets of conductance eigenvalues.

Figure 2:
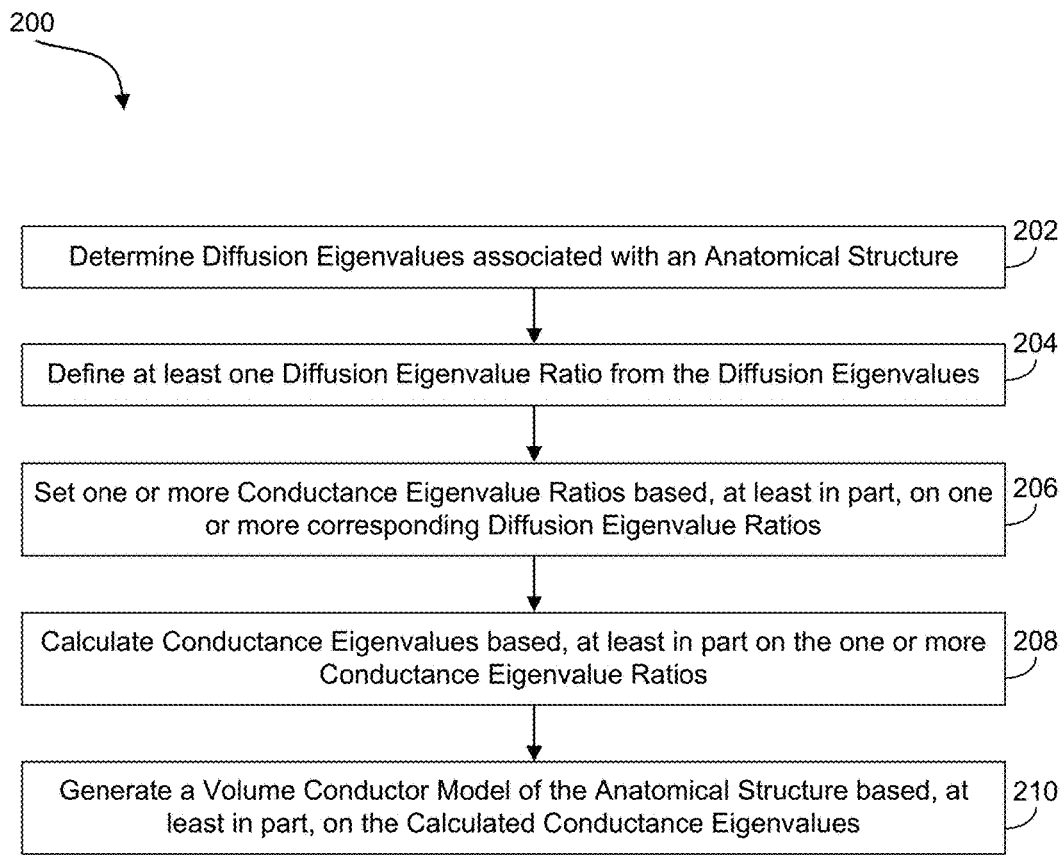
FIG. 2 illustrates an example method associated with defining the electrical properties of a volume-conductor model including steps for defining eigenvalues of a conductivity tensor based on eigenvalues of diffusion tensor.

FIG. 2 illustrates an example method 200 associated with a volume-conductor model of an anatomical structure. At 202, diffusion eigenvalues of a diffusion tensor associated with an anatomical structure are determined. The diffusion eigenvalues of the diffusion tensor characterize the diffusion of water in three orthogonal directions (i.e., the eigenvectors) within the anatomical structure. The diffusion eigenvalues of the diffusion tensor are used because the diffusion characteristics, which are based on the microstructure of an anatomical region of the anatomical structure, may vary based on parameters such as position and angular frequency.

A diffusion tensor field includes a plurality of diffusion tensors. In one embodiment, the diffusion tensor field is determined from previously sourced information, such as a database or atlas. In another embodiment, the diffusion tensor field may be determined based on imaging data regarding the anatomical structure. The imaging data may be derived from MR images from an individual patient, making the diffusion tensor field patient-specific. Where the diffusion tensor field is based on imaging data, the diffusion eigenvalues or diffusivities in a given unit of the imaging data, such as a voxel, may be determined from the diffusion tensor associated with a specific voxel. In the examples described below, the anatomical structure will be described as a brain although the method 200 may apply to other anatomical structures.

At 204, diffusion eigenvalue ratios are defined from the diffusion eigenvalues of the diffusion tensor associated with the anatomical structure. Suppose that, at 202, the eigenvalues of the diffusion tensor for a given voxel associated with the anatomical structure are determined to be $d_1$, $d_2$, $d_3$. At 204, the diffusion eigenvalue ratios may then be defined as $w_{12}=d_1/d_2$ and $w_{13}=d_1/d_3$.

At 206, ratios of conductance eigenvalues of a conductivity tensor, $\Sigma$, are set, at least in part, to one or more ratios of the diffusion eigenvalues of the diffusion tensors. In one embodiment, the conductance eigenvalues of the conductivity tensor, $\Sigma$, (i.e., $\sigma_1$, $\sigma_2$, and $\sigma_3$) are set based on the ratios of the diffusion eigenvalues and the conductance eigenvalues of the diffusion tensor, D, and the conductivity tensor, $\Sigma$, being the same. That is, $d_1/d_2=\sigma_1/\sigma_2=w_{12}$, $d_1/d_3=\sigma_1/\sigma_3=w_{13}$.

At 208, conductance eigenvalues of the conductivity tensor, $\Sigma$, are then calculated based, at least in part, on the one or more eigenvalue ratios of the conductivity tensor, $\Sigma$. For example, the conductance eigenvalues of the conductivity tensor, $\Sigma$, may be defined based on the following:

$$\sigma_1 = \sigma_{iso}\theta(w_{12}, w_{13}) \quad \text{(Eq. 1)}$$

$$\sigma_2 = \sigma_{iso}\theta(w_{12}, w_{13})w_{12}^{-1} \quad \text{(Eq. 2)}$$

$$\sigma_1 = \sigma_{iso}\theta(w_{12}, w_{13})w_{13}^{-1} \quad \text{(Eq. 3)}$$

where $\theta$ is a scalar function of the weights, $w_{12}$ and $w_{13}$. In one embodiment, $\theta$ is calculated numerically by constructing an FEM model of a spherical shell with an inner and outer radius of 1 mm and 100 mm, respectively. The inner and outer surface of the model are set to 1V and 0V, respectively; and a binary search algorithm (tolerance<1%) may be used to find a conductivity tensor, $\Sigma$, that yields the same current as the spherical shell with an isotropic tensor, $\sigma_{iso}$. Accordingly, the conductivity tensor, $\Sigma$, is parameterized by its largest conductance eigenvalue, $\sigma_1$, the ratio of $\sigma_1$ to $\sigma_2$ (i.e., $w_{12}$), and the ratio of $\sigma_2$ to $\sigma_3$ (i.e., $w_{13}$).

Figure 3:
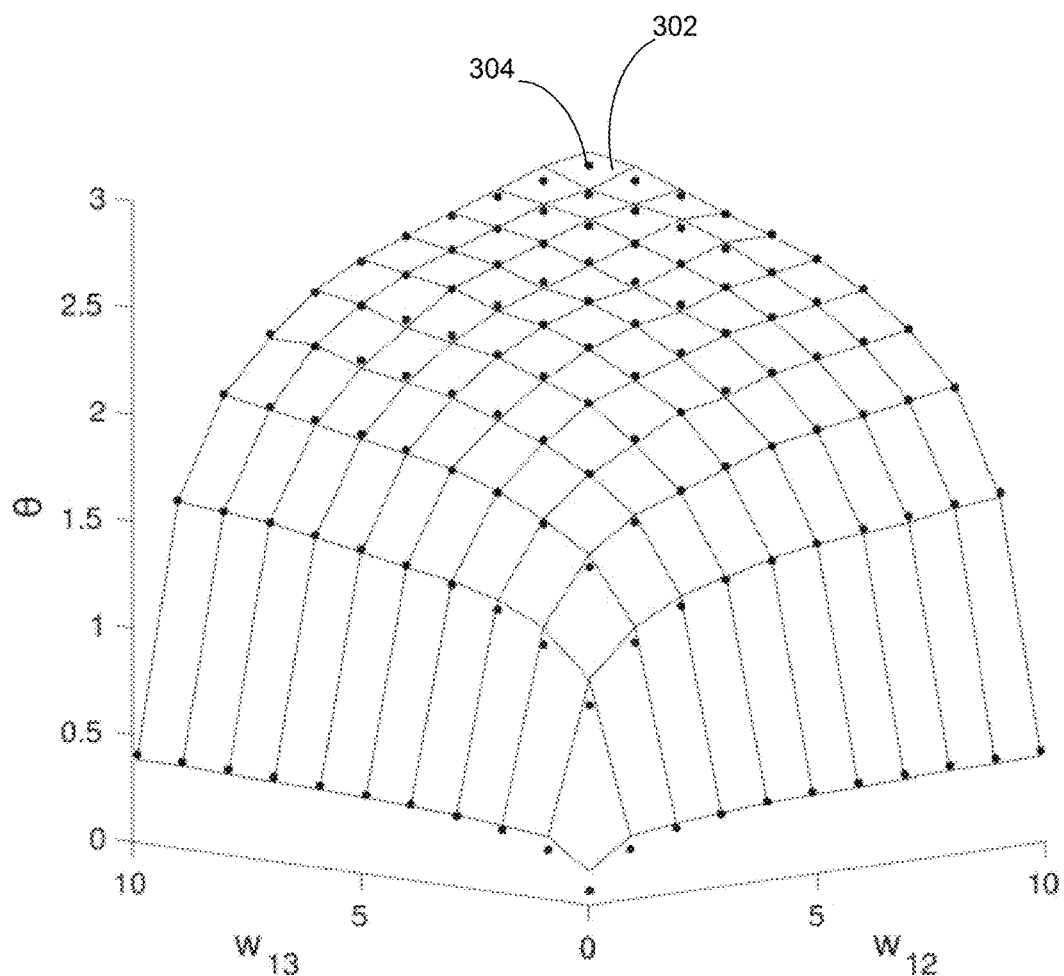
FIG. 3 illustrates one embodiment of data associated with defining the electrical properties of a volume conductor model.

Referring now to FIG. 3, an example of surface data according to an analytical fit associated with defining anisotropy in a volume-conductor model of the anatomical structure is illustrated. In particular, the relation of the $w_{12}$ and $w_{13}$ to $\theta$ for both the surface data as compared to the fit is illustrated. The surface data is represented by the rhomboid shaped surface data units, such as surface data unit 302. The analytical fit is represented by the dots, such as dot 304. Accordingly, as shown by the fit surface data relative to the analytical fit, the calculation of the conductance eigenvalues, $\sigma_1$, $\sigma_2$, and $\sigma_3$, can be constrained by a fitted model based on patient-specific information.

Now returning to FIG. 2, at 210, a volume-conductor model of the anatomical structure is constructed based, at least in part, on the calculated conductance eigenvalues of the conductivity tensor, $\Sigma$.

Figure 4:
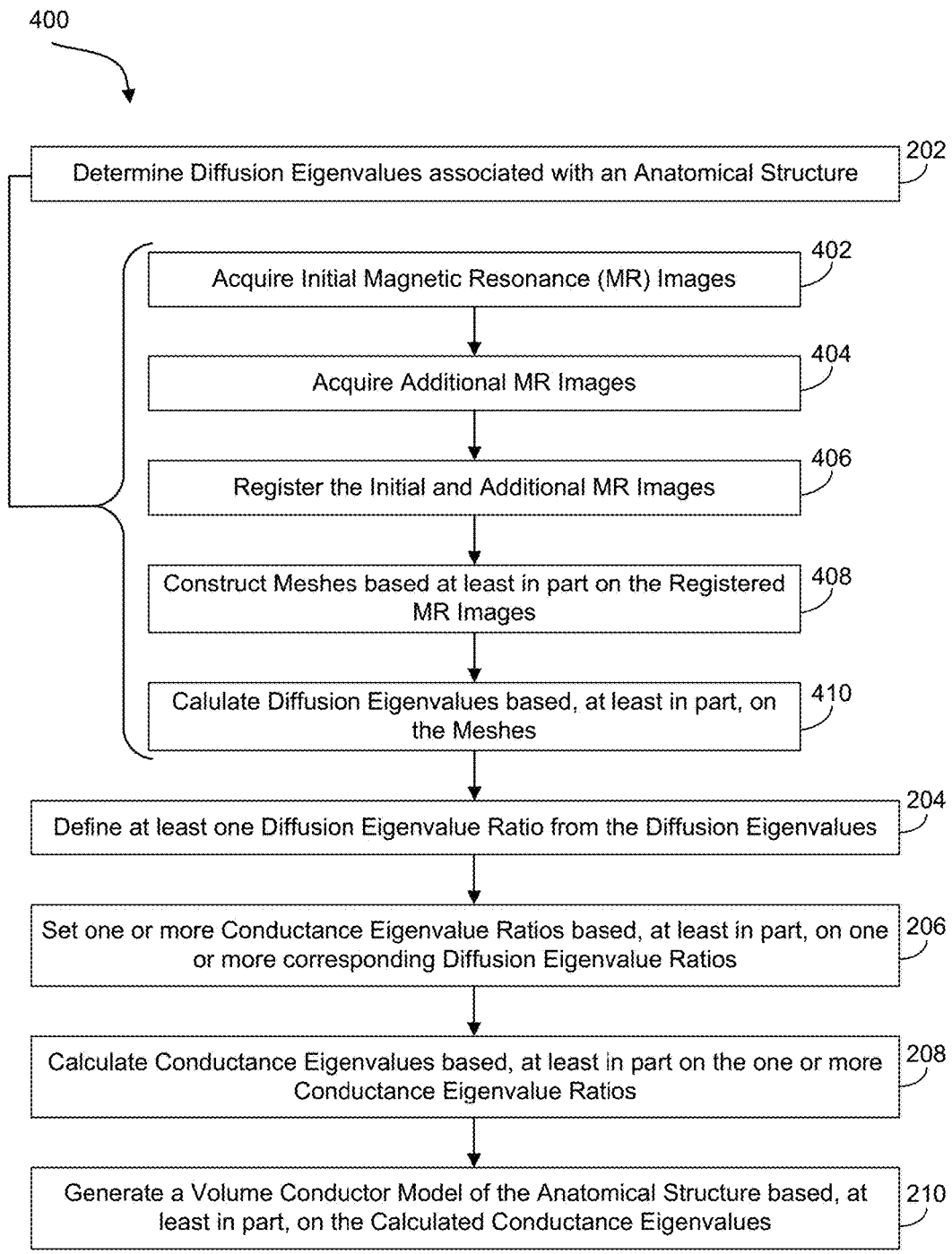
FIG. 4 illustrates an example method associated with defining the electrical properties of a volume-conductor model based on imaging data.

FIG. 4 illustrates an example method associated with defining the electrical properties of a volume-conductor model based on imaging data. In FIG. 4, steps 202, 204, 206, 208, and 210 operate as described above with respect to FIG. 2. Steps 402, 404, 406, 408, and 410 describe example steps for determining diffusion eigenvalues associated with the anatomical structure based, at least in part, on imaging data. Generally, MR images may be acquired in a specific manner so that eigenvalues of diffusion tensor field (or collection of Ds) can be determined from the imaging data. The imaging data may be received from registered MR images of initial images and additional images.

At 402, the initial images are acquired. The initial images may be T1-weighted MR images. T1 weighted (also referred to as "spin-lattice" relaxation time) images are the result of one of a pulse sequences in MR imaging. The T1-weighted MR images may be acquired using a 12-channel head matrix coil with a maximum gradient magnetic field strength of 40 mT/m. In particular, the T1W images may be acquired using a magnetization-prepared 180 degrees radio-frequency pulses and rapid gradient-echo (MPRAGE) having field of view=224 mm×256 mm×176 mm, relaxation time=2600 ms, echo time=3.02 ms, fractional anisotropy=8°, and have a generalized auto-calibrating partially parallel acquisition (GRAPPA) factor=2.

At 404, additional MR images are acquired. The additional MR images may be acquired based on the anatomical structure being modeled in the volume-conductor. Suppose that the anatomical structure is a brain. Diffusion-weighted MR images use diffusion of water in certain directions to weight the image, and this information can be used to estimate the locations and trajectories of residing groups of residing axons/fiber bundles. Accordingly, in addition to the T1W images initially acquired, diffusion-weighted images may also be acquired. The examples given below will specifically discuss diffusion-weighted images although other types of MR images will be additionally or alternatively used. For example, additional T2-weighted (T2W) MR images may be acquired.

In one embodiment, diffusion-weighted images may be acquired using a diffusion-weighted single-shot spin-echo sequence with the following parameters: a b-value of 1000 s/mm$^2$, voxel resolution=2 mm×2 mm×2 mm, 64 slices with 128 phase encoding steps and 128 frequency encoding steps, and 64 non-collinear directions with two averages. Diffusion-weighted MR images may also undergo (b-vector) corrections for motion artifacts as well as eddy current and susceptibility corrections.

At 406, the additional images are registered to the initial image so that all images are in a common space. Both the initial images and additional images contain basic units of imaging data called voxels. Voxels represent three-dimensional (3D) data associated with the anatomical structure. Accordingly, the imaging data may be volumetric imaging data. Registering the images links the data of the additional images to the initial images. For example, suppose that the initial images are T1W images and the diffusion-weighted images are the additional images. The diffusion weighted images are registered to the T1W image such that a voxel of the diffusion weighted images are linked to a corresponding voxel in the T1W image. The imaging data can then be used define the anatomical structure and possibly adjacent structures.

Figure 5A:
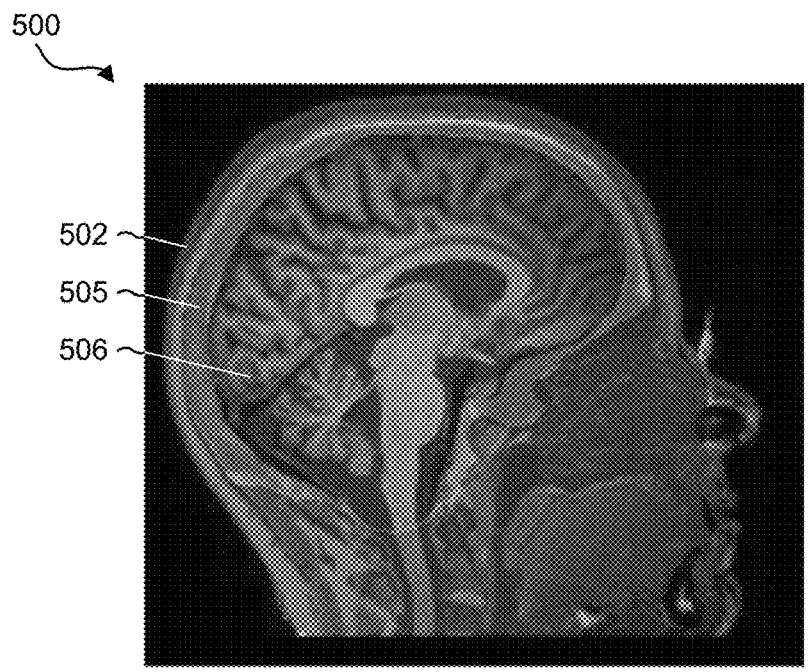
FIG. 5A segmented magnetic resonance image used for delineating the brain (red), the part of the skull that surrounds the brain (green), and soft tissues (blue) in a volume-conductor model of a patient's head.

Referring now to FIG. 5A, suppose that the anatomical structure being imaged is the head of a patient. The head may be segmented into regions. Here, the registered image 500 is subdivided into a lumped soft-tissue region 502, the portion of the skull that surrounds the brain 504, and the brain 506 based on the initial and additional images co-registered to the initial image 500. In one embodiment, a T2W MR image may be used to delineate a lumped soft-tissue region 502 the portion of the skull 504 that surrounds the brain. Furthermore, the T1W MR image may be used to delineate the brain 506.

Figure 5B:
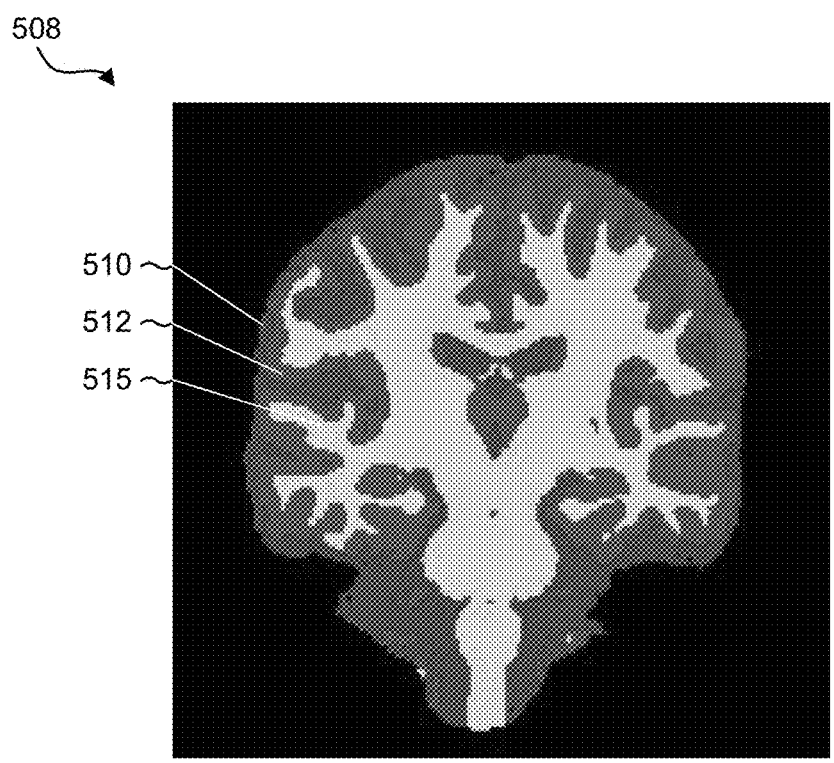
FIG. 5B segmented portion of magnetic resonance image used for delineating grey matter (red), white matter (yellow), and cerebral spinal fluid (blue) in a volume-conductor model of a patient's head.

As discussed above, any resulting volume-conductor model is complicated by heterogeneity and anisotropy in the brain. Accordingly, in FIG. 5B a segmented image 508 is derived from the co-registered image 500. In the example of the anatomical structure, the brain is subdivided into CSF (blue) 510, grey matter (red) 512, and white matter (yellow) 514. In one embodiment, the T1W image discussed above with respect to FIG. 2 was used to subdivide the co-registered image 500.

In another embodiment, voxels were classified as either CSF, white matter, or grey matter based on the tissue type that was predicted to fill the largest volume fraction within each cubic region/voxel. Additionally, mathematical methods may be used to subdivide component structures of the anatomical structure. In the example of the brain, subcortical structures, including the thalamus, pallidum, caudate, putamen, and brainstem may be further segmented using an atlas and image processing libraries and/or methods. Other mathematical models or tools may be used to segment the cortex into different cortical regions.

In DBS, a common target for Parkinson's disease is the subthalamic nucleus (STN). For example, effective subthalamic DBS for Parkinson's disease has typically used electrode contacts residing near the dorso-lateral STN. Accordingly, localization of the STN may also be determined by co-registering the segmented image 500 with an atlas of subcortical structures. In one example, a nine-parameter affine transformation with 3 translations, 3 rotations, and 3 scaling factors is used to warp the original image to a common atlas space based on the locations of the thalamus, pallidum, caudate, and putamen, which are previously delineated in both spaces. Then one can co-register a probabilistic volume of an STN to the common atlas, and the inverse transform between the original image 500 and the common atlas may be used to define the STN in the original image 500. The location of the STN may be used to place a source of electrical charge (e.g., an electrode array) within the volume-conductor model.

Returning now to FIG. 4, at 408, surface meshes are constructed based on the volumes segmented from the co-registered MR images. Suppose the anatomical structure is a brain; the surface meshes define the boundaries of the anatomical structure(s), such as the outer surface of the brain, the inner and outer surfaces of the skull, and the outer surface of a lumped soft-tissue region. A surface mesh is tessellated surface made up of a number of (typically triangular or quadrilateral) faces organized into a structured or unstructured grid. A sequence of filters can be applied to the surface meshes. For example, a filter may be used to reduce the number of faces and/or smooth the mesh. In one embodiment, the filters are applied serially until the mesh has a predetermined number of faces. In such an embodiment, a quadratic edge collapse determination, for example, is used to reduce the number of faces. Additionally, or alternatively, a Laplacian smooth with feature-preservation may be used to smooth the decimated mesh.

In one embodiment, a 4-8 subdivision rule may be used to convert the triangular mesh into a quadrilateral mesh. The surface mesh can then be used to construct a volume representing the anatomical structure, such as, the brain, the part of the skull surrounding the brain, and a lumped soft-tissue region.

At 410, conductance eigenvalues of the conductivity tensor, $\Sigma$, are calculated based, at least in part, on the meshes constructed from the imaging data. The meshes delineate different regions in the anatomical structure. Before calculating the conductance eigenvalues of the conductivity tensor, $\Sigma$, a number of other electrical properties may also be considered. For example, one electrical property that may be considered is permittivity. As an example, one may assume that the permittivity ($\varepsilon$) of grey matter and white matter, is homogeneous and isotropic. The dependence of the electrical properties on frequency in tissue regions, with the possible exception of the CSF, may be modeled using relaxation equations including Cole-Cole relaxation equations. The CSF may be deemed purely conductive (i.e., $\varepsilon=0$), meaning its conductivity is real-valued and independent of frequency.

After the conductivity tensor, $\Sigma$, and permittivity, $\varepsilon$, are defined, tetrahedral meshes are constructed within the volumes delineated by the surface meshes, and the union of all tetrahedral meshes defines the volumetric mesh within the volume-conductor modeling the head. Then, the finite element method (FEM) can be used to solve Laplace's equation for the electric potentials ($\Phi$) throughout the head:

$$\nabla \cdot (\Sigma\{\omega,x,y,z\}+j\omega\varepsilon\{\omega\}] \cdot \nabla \Phi)=0 \quad \text{(Eq. 4)}$$

In Eq. 4, $\Sigma$ is a conductivity tensor that depends on the angular frequency, $\omega$, and position; and $j$ is an imaginary unit. A scalar conductance, $\sigma$, is the degenerate form of an isotropic conductivity tensor. Additionally, the interface between the electrodes and tissue, known as the electrode-tissue interface (ETI) and the dura and arachnoid maters may be considered. For example, the ETI dura mater, and arachnoid mater were modeled using thin boundaries subject to continuity $$n \cdot \sigma^* \cdot \nabla \Phi=(\sigma_b+j\omega\varepsilon_b) \cdot h^{-1} \cdot (\Phi_1-\Phi_2) \quad \text{(Eq. 5)}$$

where h is the thickness of the boundary, $\Phi_1$ and $\Phi_2$ are the potentials on either side of the boundary, and b is a subscript denoting a property of the boundary. The Faradaic resistance ($r_f=h/\sigma_b$) and double-layer capacitance ($c_{dl}=\varepsilon_b/h$) of the ETI were set to be 150 $\Omega\text{cm}^2$ and 30 $\mu\text{F/cm}^2$, respectively. The dura and arachnoid mater were considered purely resistive ($\varepsilon_b=0$) boundary with a conductivity of 0.03 S/m. The h of the lumped dura and arachnoid layer was 2.3 mm, the median distance between the surface meshes that defined the outer brain and inner skull. A fixed potential of 1V can then be imposed on the active contact, and no current is considered to pass through the outer surface of the head, except at the inferior boundary of the head (i.e., the neck), which would have a fixed potential of 0V.

In one embodiment, the FEM may be solved using a Fourier-based approach. For example, Eq. 4 may be solved for 1025 frequencies uniformly spaced between 0 and 51.2 kHz. At these frequencies, the discrete Fourier transform (DFT) coefficients of the applied voltage waveform versus time are calculated, the solutions of Eq. 5 are scaled by the corresponding DFT coefficients and the inverse DFT applied to each node in the volumetric mesh is used to calculate the spatiotemporal distribution of potentials in the head. In one embodiment, the model may be solved using 406,335 third-order elements, which amounted to ~1.9 million degrees of freedom. In this embodiment, refinement of the volume mesh changed the interpolated potentials and subsequent stimulation thresholds by <1% with respect to the same values prior to refinement. In this manner, the FEM approach may be used to calculate the electric potentials within a volume-conductor models whose electrical properties, in part, where defined using the data derived from MR images. While the FEM approach is described, alternative or additional approaches may be used to solve Eq. 5.

The potential field generated in the anatomical structure is modeled according to an applied stimulus. In one embodiment, the stimulus is applied with an electrode having a number of electrical contacts. In some methods and systems, the electrode is an array of four cylindrical electrodes, where each electrode is 1.5 mm in height, 0.635 mm in radius, and spaced apart, from edge-to-edge, by 1.5 mm. The electrical array may be implanted in the anatomical structure, for example in the right STN. The electrical array may be placed so that the at least one contact is near the ventral boundary of the STN and another contact is near the dorsal boundary of the STN. The shaft of the electrode may be oriented to reflect surgical trajectories typically used in subthalamic DBS for the treatment of Parkinson's disease.

The method 400 continues at 204, discussed above with respect to FIG. 2, where, at each voxel, the ratios of the conductance eigenvalues are determined from the diffusion eigenvalues of the diffusion tensor, D, which characterizes diffusion in the associated anatomical structure. The bioelectric field in the anatomical structure depends on the conductivity tensor field, or collection of conductivity tensors across all voxels, and each conductivity tensor, $\Sigma$, is characterized by its associated conductance eigenvalues and conducatance eigenvectors.

Because the diffusion eigenvalues of the diffusion tensor, D, in each voxel, are determined from MR images of the patient, described at steps 402-410, the diffustion eigenvalues of the diffusion tensor, D, are patient-specific. Furthermore, because the conductance eigenvalues of the conductivity tensor, $\Sigma$, in each voxel, are determined from the diffusion eigenvalues of the diffusion tensor, D, the conductance eigenvalues of the conductivity tensor, $\Sigma$, are also patient-specific and fundamental to the construction the patient's volume-conductor model.

FIG. 6A illustrates a visual representation 600 of conductivity tensor field generated in accordance with the method 400 of FIG. 4. The visual representation 600 is comprised of a number of ellipsoids, such as unit 602 whose center is coincident with the center of a corresponding voxel in an MR image. Each unit 602 has volume that is a function of the conductance eigenvalues of the conductivity tensor, $\Sigma$, and an orientation the depends on the conductance eigenvectors of the conductivity tensor, $\Sigma$. Accordingly, the volume and orientation of each of the units is different due to changes in anisotropy and heterogeneity throughout the anatomical structure. Furthermore, the visual representation 600, may also illustrate a foreign body 604, or electrode array. The foreign body 604 may serve as a visual landmark relative to the anatomical structure.

FIG. 6B illustrates a conductivity tensor field 606 constructed using one conventional approach, the Tuch CPR Tuch. As discussed above, Tuch CPR markedly overestimates the values of the electrical properties in grey matter and white matter. Therefore, the units are so large that they overlap with each other, such as units 608.

FIG. 6C illustrates a conductivity tensor field 610 constructed in accordance with another conventional approach. The tensor field 610 accounts for heterogeneity and anisotropy; but within grey matter, white matter, and CSF, anisotropy does not change as a function of position. Therefore, the eigenvectors within the aforementioned regions can change with position, but the eigenvalues for all $\Sigma$s are all the same.

FIG. 6D illustrates a conductivity tensor field 614 constructed using a volume-conservation approach. In this approach the $\Sigma$ is defined so that its volume is the same as an effective isotropic tensor characterized by $\sigma_{iso}$, rather than defining the conductivity tensor, $\Sigma$, so that the electrical load of an infinite conductive medium is the same in both the isotropic and anisotropic cases. Although the conductivity tensor field 614 is similar, visually, to the tensor field 610 constructed using the load-preservation approach, the former is only a heuristic and is not based on principles of electrical conduction.

Figure 7:
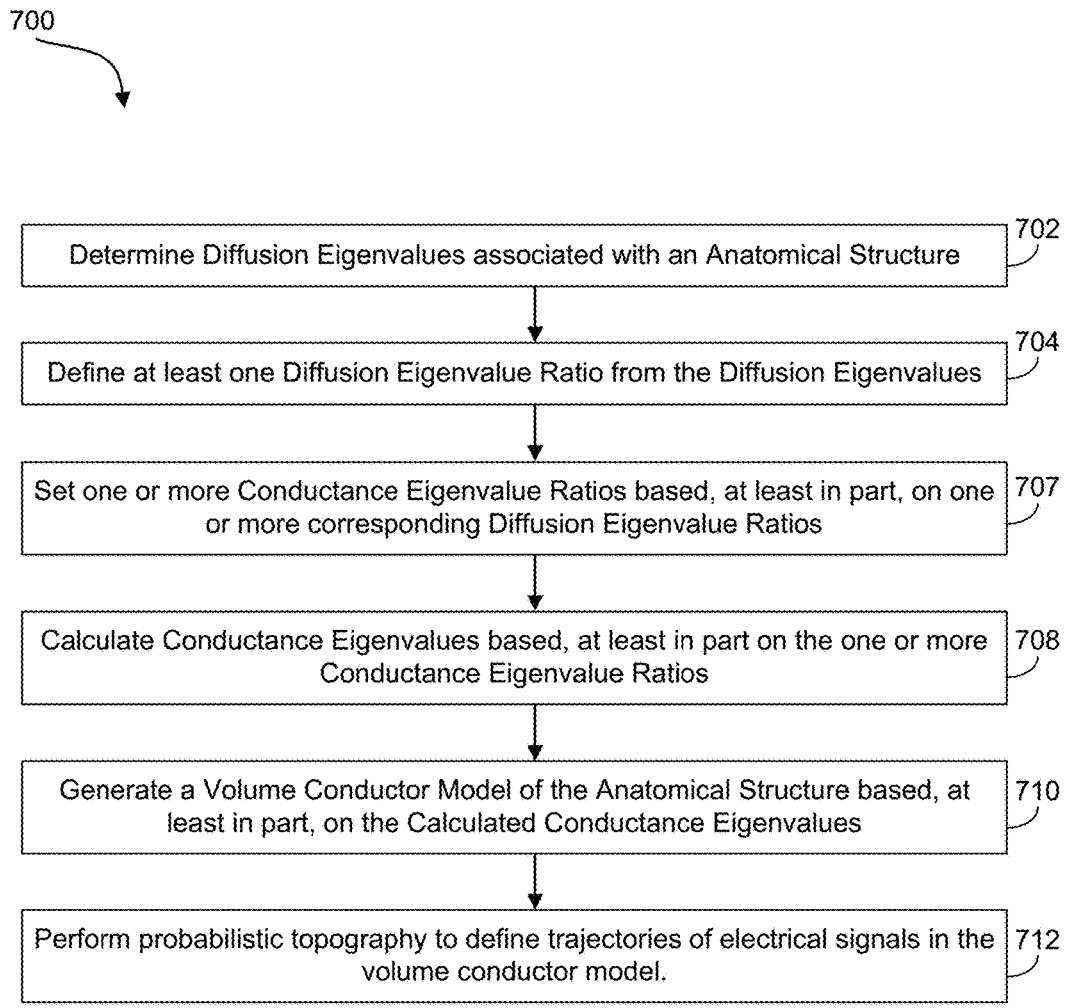
FIG. 7 illustrates an example method associated with conducting probabilistic tractography in a volume-conductor model of a human head.

FIG. 7 illustrates an example method associated with volume conductor modelling of an anatomical structure. Steps 702, 704, 706, 708, and 710 correspond to 202, 204, 206, 208, and 210 respectively, and proceed in a similar manner. Additionally, at 712, probabilistic tractography is performed to define the trajectories of electrical signals in the volume conductor model. In some embodiments, the probabilistic tractography is used in conjunction post processing processes. In the example in which the anatomical structure is a brain, the combination of probabilistic tractography and the post-processing processes may define the trajectories of axons in the corticospinal tract (CST).

In one embodiment, diffusion parameters in each voxel of a diffusion weighted image, as discussed above with respect to FIG. 4, may be estimated. Subsequently, streamlines that define electrical pathways are constructed. For example, a streamline may connect an area in the brain stem to an area in the right motor cortex. In one embodiment, streamlines may be generated for each voxel based, at least in part, on predetermined criteria. For example, waypoint and termination criterions may be that the streamlines passed through and terminated in the brainstem. Additionally or alternatively, exclusion criterion may be used. For example, exclusion criterion dictates that the streamlines could not pass through the basal ganglia structures, CSF, or right hemisphere. Thus, waypoint, termination, and exclusion criterion may define areas where a streamline should and should not pass.

The output from probabilistic tractography may be a volume density of the number of streamlines that passed through each voxel in space, known as a connectivity distribution. A weighted smoothing spline can then fitted to the connectivity distribution, using the density of streamlines at each point in space as the weights. For example, ellipses along the length of smoothing spline may be used to define the boundaries of the CST. Sets of random points can then be uniformly distributed in each of the ellipses, such that the points were connected so that the axons maintained their topographical organization across all ellipses.

The probabilistic tractography, of 712, may also include use of a simulation environment to implement cable models of myelinated axons. The simulation environment may incorporate a validated model of a mammalian motor axon and adjusted its geometry to reflect better the geometry of axons found in the brain. Axons of cortical neurons have a fiber diameter (i.e., axon diameter+myelin thickness) that ranges from 1-10 $\mu$m, the majority of which are predicted to be between 1 and 4 $\mu$m, and probability distributions of fiber diameters in some major fiber bundles in the brain are maximal between ~2 and 4 $\mu$m. Thus, a fiber diameter of 3 $\mu$m may be used to model CST. Empirical relationships between fiber diameter and other geometrical properties of the axon have been well-studied. Fourth order polynomials can be used to reproduce the empirical relationships summarized in; and, in turn, the polynomials were used to extrapolate all other geometrical parameters except the intermodal length and length of the paranodal segment. For the diameter, the relationship between fiber diameter and intermodal length may be linear, and the length of the paranodal segment was 4% of the intermodal length. Accordingly, probabilistic tractography may be used to further define the electrical properties of a volume conductor model by identifying specific electrical pathways.

Figure 8:
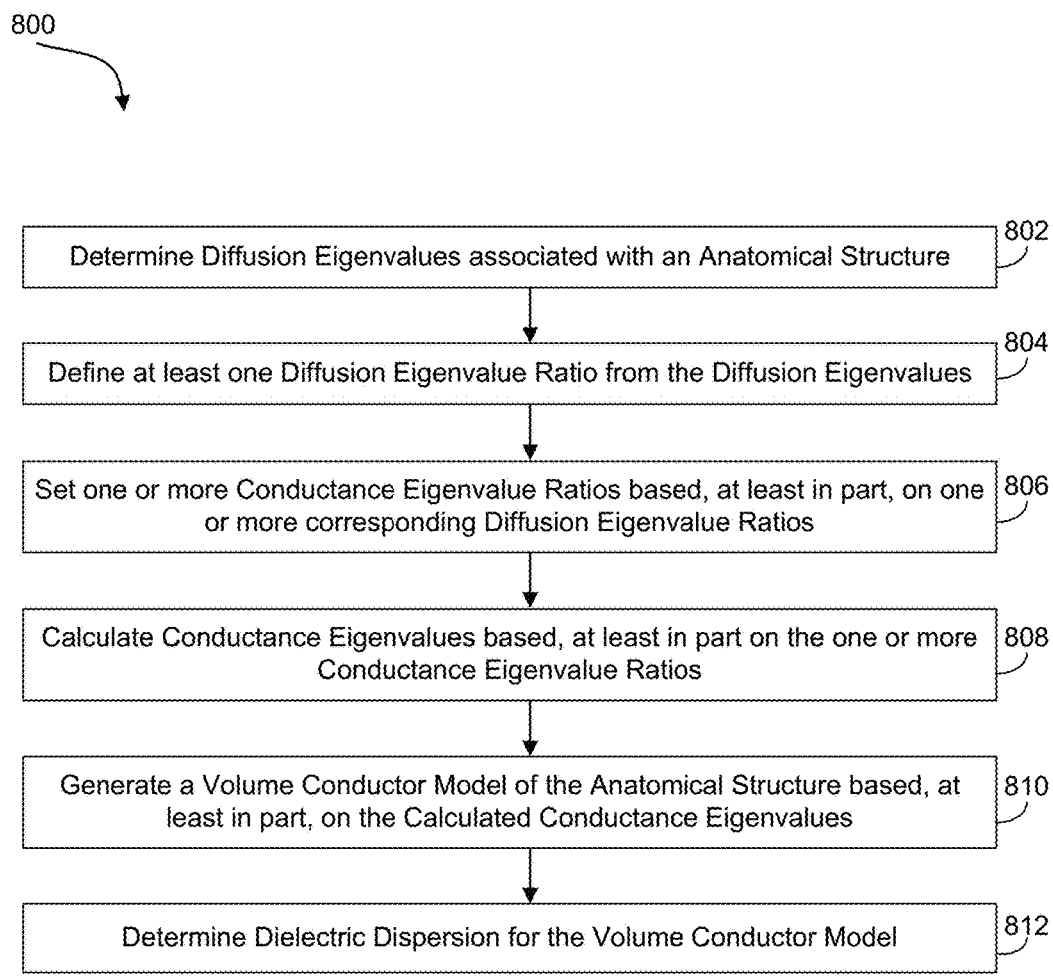
FIG. 8 illustrates an example method associated with defining dielectric dispersion in a volume-conductor model.

FIG. 8 illustrates an example method associated with volume conductor modelling that includes dielectric dispersion. Steps 802, 804, 806, 808, and 810 correspond to 202, 204, 206, 208, and 210 respectively, and proceed in a similar manner. Additionally, at 812, dielectric dispersion for the volume conductor model is determined.

Dielectric dispersion can affect the electric potentials generated in an anatomical structure, for example, during DBS. In one embodiment, a forward Fourier FEM approach is used to determine dielectric dispersion. For example, an equivalent $R_a$ of 1.03 kΩ can be calculated, which falls within the range of loads measured clinically in subthalamic DBS. Calculating the spatiotemporal distribution of potentials can be calculated by solving the FEM model at a number of frequencies. Accordingly, the effect of dielectric dispersion can incorporated in volume-conductor model.

Figure 9:
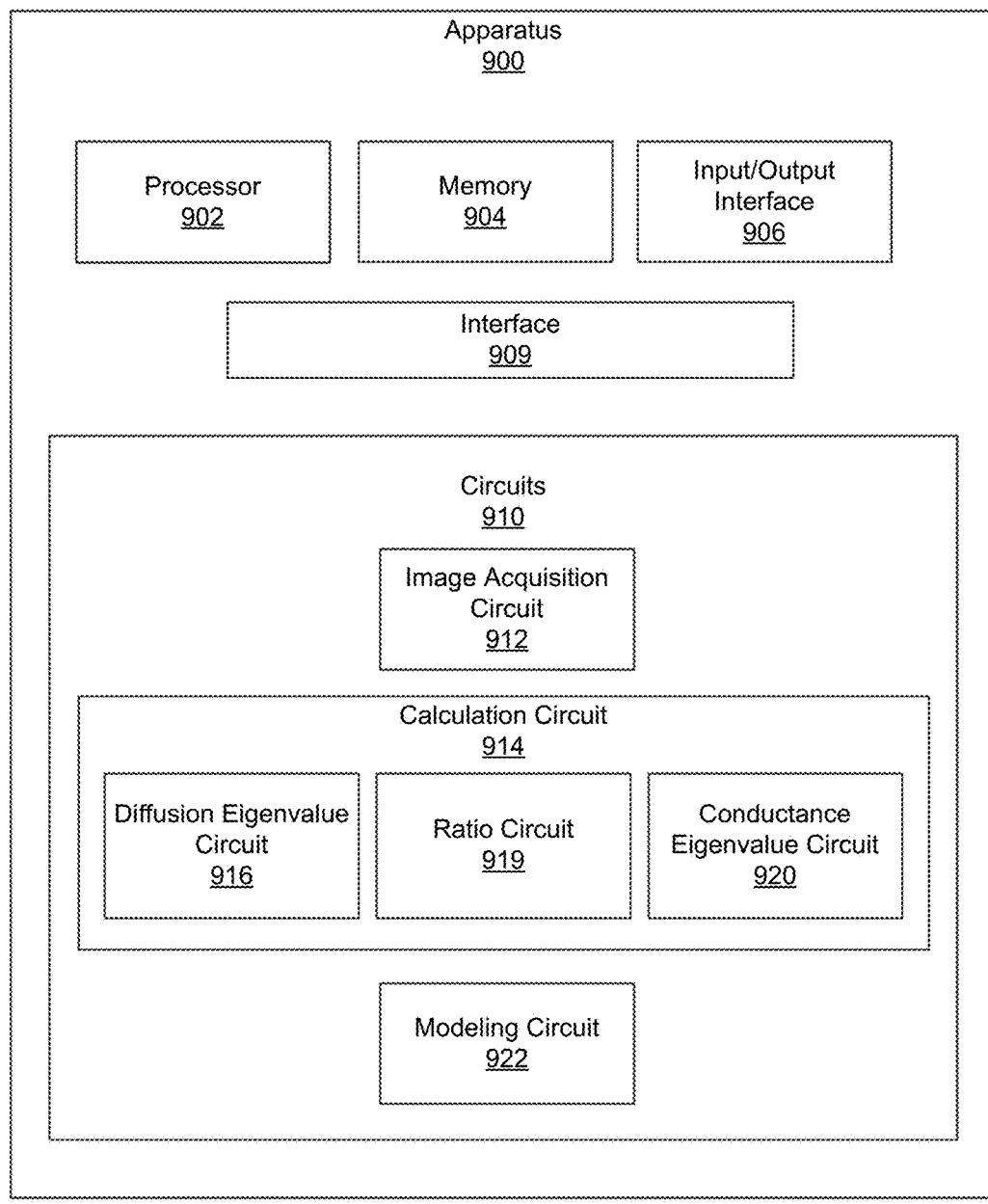
FIG. 9 illustrates an example system that generates volume-conductor models.

FIG. 9 illustrates an example system 900 for modeling conduction in a volume, such as a head. System 900 includes a processor 902, a memory 904, an input/output (I/O) interface 906, an interface 908, and a set of circuits 910. The interface 908 connects the processor 902, the memory 904, the I/O interface 906, and the set of circuits 910. The set of circuits 910 includes an image acquisition circuit 912, a calculation circuit 914, and a modeling circuit 922. The calculation circuit 914 includes a diffusion eigenvalue circuit 916, a ratio circuit 918, and a conductance eigenvalue circuit 920.

In one embodiment, the functionality associated with the set of circuits 910 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 910 are implemented as ASICs or SOCs.

The image acquisition circuit 912 acquires an image of an anatomical structure having imaging data. The image may be acquired from, for example, a CT or MR apparatus. The anatomical structure may be a region in a patient's body. For example, the image of the region of tissue may include an image of a brain, which can be used to delineate the STN or other regions of interest. In one embodiment, a slice of a volumetric image is a 1 mm to 5 mm thick. The images are formed from a plurality of voxels that represent 3D units of the anatomical structure. Collectively the voxels form the imaging data. Other imaging approaches may be used to generate and access the image accessed by the image acquisition circuit 912. Other image modalities, dimensions, pixel sizes, or resolutions may also be used.

The calculation circuit 914 uses the imaging data from the image acquisition circuit 912 to calculate the conductance eigenvalues of a conductivity tensor. In particular, the diffusion-eigenvalue circuit 916 calculates diffusion eigenvalues of a diffusion tensor at each voxel in the imaging data. Each voxel is associated with a diffusion tensor, so set of diffusion eigenvalues can be calculated for each voxel from the imaging data.

The ratio circuit 918 defines one or more diffusion ratios of the diffusion eigenvalues of the diffusion tensors calculated by the diffusion-eigenvalue circuit 916. The ratio circuit sets one or more ratios of the conductance eigenvalues of the conductivity tensor based, at least in part, on one or more corresponding diffusion ratios of diffusion eigenvalue of the corresponding diffusion tensor. The correspondence of the diffusion eigenvalues of the diffusion tensor may be passed to the conductance eigenvalues of the corresponding conductivity tensor in a given voxel of imaging data. In another embodiment, the correspondence between the diffusion eigenvalues of the diffusion and conductivity tensors may be predetermined.

The conductivity tensor, $\Sigma$, is constructed from conductance eigenvalues and eigenvectors. For each voxel, the diffusion ratios of the diffusion eigenvalues in both the diffusion tensor, D, and the conductivity tensor, $\Sigma$, may be the same. The conductivity tensor, $\Sigma$, may preserve an electrical load. The preservation is such that the electrical load of a homogeneous infinite medium is the same whether the medium is anisotropic with a conductivity tensor of $\Sigma$ or isotropic with a degenerate scalar conductivity of $\sigma_{iso}$.

The conductance eigenvalue circuit 920 calculates the conductance eigenvalues of the conductivity tensor, $\Sigma$, at least in part, based on the one or more of the diffusion ratios of the diffusion eigenvalues. In one embodiment, the conductance-eigenvalue circuit 920 defines an effective scalar conductance based, at least in part, on a measurement calculated in vivo from a sample of biological tissue that was assumed to be homogeneous and isotropic. The conductance-eigenvalue circuit 920 then calculates the conductance eigenvalues of the conductivity tensor, $\Sigma$, according to a scalar mapping that chooses the conductance eigenvalue of the conductivity tensor, $\Sigma$, so that a predefined electrical load is preserved. In one embodiment, the electrical load can be calculated by approximating the aforementioned biological tissue as a homogeneous, isotropic infinite medium. A continuous form of the scalar function can be approximated based, at least in part, on a nonlinear analytic expression.

The modelling circuit 922 generates a volume-conductor model using the conductance eigenvalues of the conductivity tensor, $\Sigma$. In another embodiment, the modeling circuit 922 may further identify at least one electrode target in the anatomical structure. The electrode target may be a point at which stimulation can be applied to the anatomical structure. In an embodiment in which the conductance eigenvalues of the conductivity tensor, $\Sigma$, are calculated from the patient-specific imaging data, at least one electrode target is specifically based on the patient's own anatomy, thereby increasing the specificity and potentially efficacy of treatment.

Figure 10:
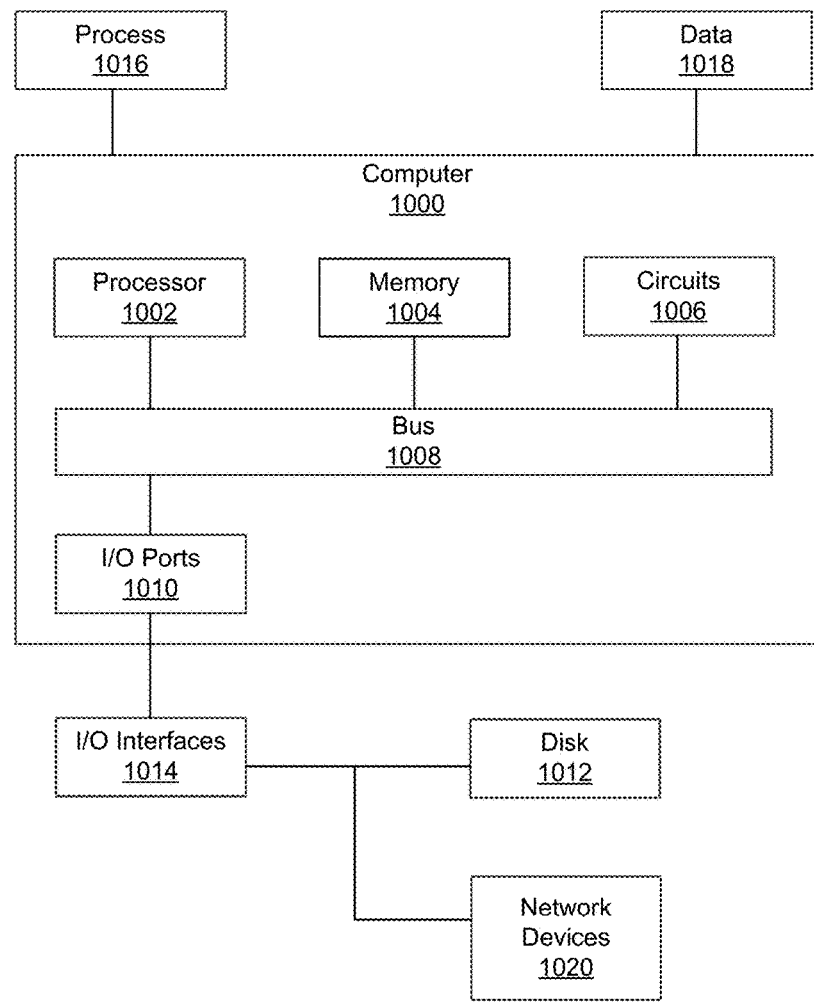
FIG. 10 illustrates an example computer in which example methods and apparatus may operate.

FIG. 10 illustrates an example computer 1000 in which example methods illustrated herein can operate and in which example circuits may be implemented. In different examples, computer 1000 may be part of a CT or MR system, may be operably connectable to a CT system, may be part of an MRI system, or may be part of a CADx system.

Computer 1000 includes a processor 1002, a memory 1004, circuits 1006 and input/output ports 1010 operably connected by a bus 1008. In one example, computer 1000 may include a set of circuits 1006 that perform a method of characterizing a nodule in a region of lung tissue. Thus, the set of circuits 1006, whether implemented in computer 1000 as hardware, firmware, software, and/or a combination thereof may provide means (e.g., hardware, software) for generating a volume conductor model. The set of circuits 1006 may correspond to the circuits 910, and thus include one or more of an image acquisition circuit 912, a calculation circuit 914, a diffusion eigenvalue circuit 916, a ratio circuit 918, a conductance eigenvalue circuit 920, and a modeling circuit 922, as described above with respect to FIG. 9.

In different examples, the set of circuits 1006 may be permanently and/or removably attached to computer 1000. In one embodiment, the functionality associated with the set of circuits 1006 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 1006 are implemented as ASICs or SOCs.

Processor 1002 can be a variety of various processors including dual microprocessor and other multi-processor architectures. Memory 1004 can include volatile memory and/or non-volatile memory. A disk 1012 may be operably connected to computer 1000 via, for example, an input/output interface (e.g., card, device) 1014 and an input/output port 1010. Disk 1012 may include, but is not limited to, devices like a magnetic disk drive, a tape drive, a Zip drive, a solid state device (SSD), a flash memory card, or a memory stick. Furthermore, disk 1012 may include optical drives like a CD-ROM or a digital video ROM drive (DVD ROM). Memory 1004 can store processes 1016 or data 1018, for example. Disk 1012 or memory 1004 can store an operating system that controls and allocates resources of computer 1000.

Bus 1008 can be a single internal bus interconnect architecture or other bus or mesh architectures. While a single bus is illustrated, it is to be appreciated that computer 1000 may communicate with various devices, logics, and peripherals using other busses that are not illustrated (e.g., PCIE, SATA, Infiniband, 1394, USB, Ethernet).

Computer 1000 may interact with input/output devices via I/O interfaces 1014 and input/output ports 1010. Input/output devices can include, but are not limited to, digital whole slide scanners, a CT machine, an optical microscope, a keyboard, a microphone, a pointing and selection device, cameras, video cards, displays, disk 1012, network devices 1020, or other devices. Input/output ports 1010 can include but are not limited to, serial ports, parallel ports, or USB ports.

Computer 1000 may operate in a network environment and thus may be connected to network devices 1020 via I/O interfaces 1014 or I/O ports 1010. Through the network devices 1020, computer 1000 may interact with a network. Through the network, computer 1000 may be logically connected to remote computers. The networks with which computer 1000 may interact include, but are not limited to, a local area network (LAN), a wide area network (WAN), or other networks.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

To the extent that the term "includes" or "including" is employed in the detailed description or the claims, it is intended to be inclusive in a manner similar to the term "comprising" as that term is interpreted when employed as a transitional word in a claim.

"Circuit", as used herein, includes but is not limited to hardware, firmware, software in execution on a machine, or combinations of each to perform a function(s) or an action(s), or to cause a function or action from another circuit, method, or system. Circuit may include a software controlled microprocessor, a discrete logic (e.g., ASIC), an analog circuit, a digital circuit, a programmed logic device, a memory device containing instructions, and other physical devices. Circuit may include one or more gates, combinations of gates, or other circuit components. Where multiple logical circuits are described, it may be possible to incorporate the multiple circuits into one physical logic or circuit. Similarly, where a single logical circuit is described, it may be possible to distribute that single circuit between multiple logics or circuits.

"Computer-readable storage medium", as used herein, refers to a non-transitory medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, a data storage device, and other media from which a computer, a processor or other electronic device can read.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method for volume conducting modelling, comprising:
   receiving diffusion eigenvalues of a diffusion tensor associated with an anatomical structure having heterogeneous, anisotropic tissue;
   determining diffusion ratios corresponding to ratios of the diffusion eigenvalues in the diffusion tensor;
   for each diffusion ratio, setting a respective conductance ratio equal to the diffusion ratio;
   calculating conductance eigenvalues of a conductivity tensor based, at least in part, on the conductance ratios; and
   generating a volume-conductor model of the anatomical structure based, at least in part, on the calculated conductance eigenvalues of the conductivity tensor, wherein the conductivity tensor preserves an electrical load of a homogeneous infinite tissue whether the tissue is isotropic or anisotropic.

2. The method of claim 1, wherein calculating the conductance eigenvalues of the conductivity tensor further comprises:
   defining a scalar conductance based on the anatomical structure; and
   calculating the conductance eigenvalues of the conductivity tensor according to a scalar function and the scalar conductance.

3. The method of claim 2 wherein a continuous form of the scalar function can be approximated based on a nonlinear analytic expression.

4. The method of claim 2, wherein the scalar conductance is a degenerate form of anisotropic tensor.

5. The method of claim 1, wherein the diffusion eigenvalues of the diffusion tensor are determined from imaging data that is derived from at least one diffusion-weighted magnetic resonance (MR) image.

6. The method of claim 1, wherein the anatomical structure is a brain having white matter, grey matter, and cerebral spinal fluid (CSF).

7. The method of claim 6, wherein the volume-conductor model represents heterogeneous or anisotropic characteristics of the white matter, the grey matter, or the cerebral spinal fluid (CSF).

8. The method of claim 1, further comprising:
   identifying at least one electrode target in the anatomical structure for stimulation based, at least in part, on the volume-conductor model.

9. A method for modeling volume conductors, comprising:
   receiving imaging data associated with an anatomical structure, wherein the imaging data is associated with a plurality of voxels, and wherein a diffusion tensor, having diffusion eigenvalues and diffusion eigenvectors, is defined for each voxel of the plurality of voxels;
   calculating a conductivity tensor for a voxel having conductance eigenvalues and conductance eigenvectors for the anatomical structure by setting ratios of conductance eigenvalues in the conductivity tensor equal to corresponding ratios of diffusion eigenvalues in a selected diffusion tensor, wherein an infinite medium, corresponding to the anatomical structure, whose electrical properties are defined by the conductivity tensor which has the same electrical load whether the infinite medium is isotropic or anisotropic; and
   generating a volume-conductor model of the anatomical structure based, at least in part, on the conductance eigenvalues.

10. The method of claim 9, wherein the conductance eigenvalues of the conductivity tensor are a first set of conductance eigenvalues, the method further comprising:
    calculating a second set of conductance eigenvalues corresponding to a different conductivity tensor.

11. The method of claim 9, wherein calculating the conductance eigenvalues of the conductivity tensor comprises:
    defining a scalar conductance based on the anatomical structure; and
    calculating the conductance eigenvalues of the conductivity tensor according to a scalar function and a scalar conductance.

12. The method of claim 11, wherein the scalar conductance is a degenerate form a spherical isotropic tensor.

13. The method of claim 9, wherein the imaging data is based, at least in part, on at least one diffusion-weighted magnetic resonance (MR) image.

14. The method of claim 9, wherein the anatomical structure is a brain having white matter, grey matter, and cerebral spinal fluid (CSF), and wherein the volume-conductor model represents heterogeneous or anisotropic characteristics of the white matter, the grey matter, or the cerebral spinal fluid (CSF).

15. The method of claim 9, further comprising:
    identifying at least one electrode target in the anatomical structure for stimulation based, at least in part, on the volume-conductor model.

16. A non-transitory computer-readable storage medium storing computer executable instructions that when performed by a computer control the computer to perform a method, comprising:
    receiving volumetric imaging data associated with an anatomical structure, wherein the imaging data is associated with a plurality of voxels, and wherein a diffusion tensor having diffusion eigenvalues and diffusion eigenvectors defined for each voxel of the plurality of voxels;
    calculating a conductivity tensor having conductance eigenvalues and conductance eigenvectors for the anatomical structure by setting ratios of conductance eigenvalues in the conductivity tensor equal to corresponding ratios of diffusion eigenvalues in a selected diffusion tensor; and generating a volume-conductor model of the anatomical structure based, at least in part, on the eigenvalues of a plurality of conductivity tensors.

17. The non-transitory computer-readable storage medium of claim 16, further comprising:

identifying a plurality of electrode targets in the anatomical structure for stimulation based, at least in part, on the volume-conductor model.

18. The non-transitory computer-readable storage medium of claim 17, further comprising:

selecting an electrode target from the plurality of electrode targets based, at least in part, on the volume-conductor model specific to the anatomical structure.

* * * * *